US011117938B2

(12) United States Patent
Chiu et al.

(10) Patent No.: US 11,117,938 B2
(45) Date of Patent: Sep. 14, 2021

(54) RNA INTERFERENCE FOR CONTROL OF INSECT PESTS

(71) Applicant: Regents of the University of California, Oakland, CA (US)

(72) Inventors: Joanna C. Chiu, Concord, CA (US); Katherine A. Murphy, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 282 days.

(21) Appl. No.: 16/061,321

(22) PCT Filed: Dec. 13, 2016

(86) PCT No.: PCT/US2016/066346
§ 371 (c)(1),
(2) Date: Jun. 11, 2018

(87) PCT Pub. No.: WO2017/106171
PCT Pub. Date: Jun. 22, 2017

(65) Prior Publication Data
US 2019/0037854 A1     Feb. 7, 2019

Related U.S. Application Data (60) Provisional application No. 62/266,862, filed on Dec. 14, 2015.

(51) Int. Cl.
| | |
|---|---|
| *A61K 48/00* | (2006.01) |
| *C07H 21/04* | (2006.01) |
| *C07K 14/435* | (2006.01) |
| *C12N 9/18* | (2006.01) |
| *A01N 63/60* | (2020.01) |
| *C12N 15/113* | (2010.01) |

(52) U.S. Cl.
CPC ........ *C07K 14/43581* (2013.01); *A01N 63/60* (2020.01); *C12N 9/18* (2013.01); *C12N 15/113* (2013.01); *C12N 2310/14* (2013.01)

(58) Field of Classification Search
CPC .......................... C12N 15/113; C12N 2310/14
See application file for complete search history.

(56) References Cited

U.S. PATENT DOCUMENTS

| | | | | |
|---|---|---|---|---|
| 8,318,474 B1 * | 11/2012 | Smolke | ............... | C07K 14/395 435/255.1 |
| 2003/0108520 A1 | 6/2003 | Borovsky et al. | | |
| 2009/0285784 A1 * | 11/2009 | Raemaekers | ...... | C12N 15/8286 424/93.2 |
| 2012/0240288 A1 * | 9/2012 | Ye | ...................... | C12N 15/8286 800/279 |
| 2014/0026255 A1 * | 1/2014 | Grunden | ............ | C12N 15/8271 800/278 |

FOREIGN PATENT DOCUMENTS

| | | | | |
|---|---|---|---|---|
| WO | WO 03/099298 A1 * | 12/2003 | ........... | C12N 15/113 |
| WO | WO 2013/156492 A2 * | 10/2013 | ........... | C12N 15/113 |
| WO | WO 2014/106838 A2 * | 7/2014 | ........... | C12N 15/113 |
| WO | 2015/153339 A2 | 10/2015 | | |

OTHER PUBLICATIONS

International Search Report and Written Opinion dated Mar. 27, 2017 in International Application No. PCT/US2016/066346, 10 pages.

Baum, J.A., et al.; "Control of coleopteran insect pests through RNA interference"; *Nature Biotechnology*; vol. 25, No. 11; Nov. 2007; pp. 1322-1326.

Zhang, J. et al.; "Full crop protection from an insect pest by expression of long double-stranded RNAs in plastids" *Science*; vol. 347, Issue 6225; Feb. 27, 2015; pp. 991-994.

\* cited by examiner

*Primary Examiner* — Amy H Bowman
(74) *Attorney, Agent, or Firm* — Kilpatrick Townsend and Stockton LLP (57) ABSTRACT

This invention provides a methods and compositions for controlling an insect pest. The methods comprise contacting the insect pest with a composition comprising a yeast cell comprising a nucleic acid encoding a dsRNA molecule which specifically inhibits expression of a target gene in the insect pest, thereby controlling the insect pest.

22 Claims, 6 Drawing Sheets
Specification includes a Sequence Listing.

RNA INTERFERENCE FOR CONTROL OF INSECT PESTS

CROSS-REFERENCES TO RELATED APPLICATIONS

This application claims priority under 35 U.S.C. § 119(e) to U.S. Application No. 62/266,862, filed Dec. 14, 2015, which is incorporated herein by reference.

FIELD OF THE INVENTION

This invention relates to methods and compositions for controlling insect pests using RNA interference.

BACKGROUND OF THE INVENTION

In recent years, RNA interference (RNAi) has shown great potential to become a powerful tool in pest management. RNAi is effective in many economically important insects, including honey bee, mosquito, Western corn rootworm, and Colorado potato beetle [1-5]. Inducing mortality through RNAi has several advantages over conventional chemical pesticides. As a consequence of its sequence dependent mode of action, RNAi can be tailored to target only pest species and spare beneficial insects[6,7]. This is accomplished by choosing to target unique mRNA sequences within the pest species. Likewise, RNAi pesticides can be designed to target a broad range of insects by choosing sequences that are more conserved between species. Another advantage of RNAi pesticides is that the "active ingredient" is RNA, which is organic, biodegradable, and can be cheaply produced within microorganisms.

RNAi is a cellular mechanism that likely evolved to protect eukaryotes from RNA viruses[8]. To activate the RNAi pathway, double stranded RNA (dsRNA) can be fed to insects and absorbed into the cells that line the midgut. Exogenous dsRNA is usually processed into 20-30 nucleotide duplexes by the ribonuclease III enzyme DICER[9]. These nucleotide duplexes are incorporated into the RNA induced silencing complex (RISC) by the catalytic component ARGONAUTE. The two strands of RNA are unwound and one strand is used as a guide strand. The guide strand binds to complementary mRNAs, and the RISC complex mediates degradation or suppression of the endogenous transcript. The RISC complex will cleave the mRNA when base pair matching is perfectly complementary, or alternatively, the complex can bind the mRNA and suppress translation when there are mismatched base pairs, leaving the mRNA intact. Degradation or suppression of transcripts that code for critical genes in the insect results in decreased amounts of critical gene products and increased mortality. [10,11]

Delivery of intact dsRNA into insect cells remains a challenge, although many delivery methods have been developed [10]. Crops can be genetically engineered to express dsRNA targeting insect pests. The use of modified plants has proven remarkably effective in managing coleopteran pests such as the Colorado potato beetle [4]. Another delivery method is to synthesize the dsRNA in vitro, and then apply to foliage by spraying [12], or to roots by soaking [13], resulting in a transient presence of dsRNA within the plant tissue. Studies have demonstrated that bacteria expressing dsRNA can be heat killed and fed to insects to induce RNAi [14], or can even be fed in a viable state so that the genetically modified bacteria can colonize the gut and deliver dsRNA from within the host [15].

Despite these advances, the prior art fails to show that other microorganisms, such as yeast, are useful as a delivery for vehicle for dsRNA. The present invention addresses these and other needs.

BRIEF SUMMARY OF THE INVENTION

This invention provides methods and compositions for controlling an insect pest. The methods comprise contacting the insect pest with a composition comprising a yeast cell (either killed or living) comprising a nucleic acid encoding a dsRNA molecule which specifically inhibits expression of a target gene in the insect pest, thereby controlling the insect pest. The compositions of the invention are typically present in a lure trap.

The yeast cell can be any yeast capable of transformation and can be, for example, *Saccharomyces cerevisiae*. The insect pest can be, for example, a vinegar fly, such as *Drosophila suzukii*. In those embodiments, yeast cell can be *Hanseniaspora uvarum*.

The target gene can be tubulin, vATPase, blw, RpL19, or acetyl choline esterase. The target sequence in the target gene can be at least about 90% identical to SEQ ID NO: 1, SEQ ID NO: 2, SEQ ID NO: 3, or SEQ ID NO: 4.

The invention also provides expression cassettes comprising a yeast promoter operably linked to a DNA sequence encoding a dsRNA which specifically inhibits expression of a target gene in an insect pest. The yeast promoter can be, for example, a constitutively active TEF1 promoter. In some embodiments, the yeast promoter is an inducible promoter. The target gene can be tubulin, vATPase, blw, RpL19, or acetyl choline esterase. The target sequence in the target gene can be at least about 90% identical to SEQ ID NO: 1, SEQ ID NO: 2, SEQ ID NO: 3, or SEQ ID NO: 4.

Definitions

The terms "nucleic acid," "polynucleotide," and "oligonucleotide" refer to a single or double-stranded polymer of deoxyribonucleotide or ribonucleotide bases read from the 5' to the 3' end. The monomer is typically referred to as a nucleotide. Nucleic acids can include modified nucleotides that permit correct read through by a polymerase and do not significantly alter expression of a polypeptide encoded by that nucleic acid.

The phrase "nucleic acid sequence encoding" refers to a nucleic acid (i.e., DNA) which is the template for transcription of a specific RNA molecule (e.g., a dsRNA) or an mRNA that is translated into a protein. The nucleic acid sequences include both the full length nucleic acid sequences as well as non-full length sequences derived from the full length sequences. A coding sequence can include degenerate codons (relative to the native sequence) or sequences that provide codon preference in a specific host cell.

The term "promoter" refers to regions or sequence located upstream and/or downstream from the start of transcription and which are involved in recognition and binding of RNA polymerase and other proteins to initiate transcription. A "yeast promoter" is a promoter capable of initiating transcription in yeast cells. A yeast promoter can be a nucleic acid sequence originally isolated from a yeast, but promoters not initially isolated from a yeast are also considered "yeast promoters" for the purposes of this disclosure.

An "expression cassette" refers to a nucleic acid construct, which when introduced into a host cell (e.g., a yeast cell), results in transcription of an RNA molecule (e.g., dsRNA or mRNA). An expression cassette typically includes a sequence to be expressed, and sequences necessary for expression of the sequence to be expressed, such as a promoter operably linked to the sequence. Generally, an expression cassette is inserted into an expression vector to be introduced into a host cell.

The term "gene" refers to a segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene (e.g., promoters, enhancers, etc.). A "gene product" can refer to either the mRNA or protein expressed from a particular gene.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity can be partial, in which only some of the nucleic acids match according to base pairing, or complete, where all the nucleic acids match according to base pairing.

The terms "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified.

The terms "identical" or percent "identity," in the context of two or more nucleic acids or proteins of the invention, refer to two or more sequences or subsequences that are the same or have a specified percentage of nucleotides or amino acids that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST/. For example, the sequence of a dsRNA of the invention can be compared using the above techniques to the sequence of a target gene in an insect pest, taking into account the presence of uracil in the dsRNA and thymidine in the DNA. Sequences that have at least about 90% sequence identity using the methods described above are said to be "substantially identical." This definition also refers to, and can be applied to, the compliment of a test sequence. The definition also includes sequences that have deletions and/or additions, as well as those that have substitutions. Optimal alignment of such sequences can be carried out by any of the publically available algorithms or programs for determining sequence identity and alignment, e.g., BLAST.

DETAILED DESCRIPTION

This invention provides evidence that genetically modified yeast can be used to produce and deliver dsRNA to an insect pest, such as vinegar flies (members of the genus Drosophila), resulting in altered gene expression and decreased fitness in the insect pest.

Target Insect Nests

The present invention can be used to control any insect pest that will naturally ingest yeast in the environment. For example, yeast is an important endosymbiont and a major component of the microbiome in Drosophila[16]. Yeasts are naturally found growing on the surface of intact and rotting vinegars and produce volatiles that are highly attractive to Drosophilids [17,18]. Palanca et al. quantified the attractive properties of wild yeast isolates and found vinegar associated isolates were more attractive than those not associated with vinegar, regardless of taxonomic positioning [19]. Additionally, they found that Saccharomyces cerevisiae was the most attractive to Drosophila melanogaster. Drosophila acquire yeast from the environment and can transmit yeast horizontally to mates [20] Drosophila-associated yeast spores can be passed intact through the gut and deposited onto food sources [21], where they can be ingested by larvae or adults. Thus, yeast is a chemoattractive, transmittable symbiont of insect pests, such as Drosophila. These characteristics make yeast an ideal and novel candidate to serve as a living biopesticide.

Drosophila suzukii, commonly known as Spotted Wing Drosophila, is an invasive pest of a variety of soft skinned vinegars [22]. Native to South East Asia, this pest was first identified in California in 2008. Since then, infestations have spread across the United States, Canada, and Europe[23], resulting in an estimated 718 million dollars in crop losses annually [24,25]. D. suzukii is sufficiently homologous to the model insect D. melanogaster to facilitate target gene selection. The D. suzukii genome has been sequenced, which further aids in the design of dsRNAs [26]. Additionally, yeast-baited traps have been demonstrated to effectively lure D. suzukii in an agricultural setting[27], and evidence suggests that D. suzukii feed on yeasts in the field[28].

Thus, the present invention is useful for control of Drosophilids (e.g., D. melanogaster, D. suzukii, D. biarmipes, D. takahashii, D. erecta, D. yakuba, D. simulans, D. sechellia, D. ananassae, D. persimilis, D. pseudoobscura, D. willistoni, D. grimshawi, D. virillis, D. subpulchrella, D. biarmipies and D. mojavensis). One of skill will recognize that other insect pests that are symbiotic with yeast can be targeted in a similar manner. A number of examples of insect-yeast symbiosis are known (see e.g., Gonzalez F (2014) Symbiosis between yeasts and insects. Introductory paper at the Faculty of Landscape Architecture, Horiculture, and Crop Production Science. 1-52). Examples of symbiosis between insects and yeast have been characterized in many of the important insect orders, including Hymenoptera (specifically wasps, bees, and ants), Coleoptera (beetles), Hemiptera (aphids and plants hoppers), Lepidoptera (Sigelgaita sp.) and Neuroptera (lacewing).

RNA Interference

RNAi strategies for reducing or inhibiting expression of a target gene are known. RNAi techniques employ genetic constructs that encode double-stranded RNA (dsRNA). Typically, the genetic constructs comprise sense and anti-sense sequences which are placed in regions flanking an intron sequence in proper splicing orientation with donor and acceptor splicing sites. Alternatively, spacer sequences of various lengths can be employed to separate self-complementary regions of sequence in the construct. During processing of the gene construct transcript, intron sequences can be spliced-out, allowing sense and anti-sense sequences, as well as splice junction sequences, to bind forming double-stranded RNA. Alternatively, where secondary structure inhibits splicing machinery, the intron sequences are not spliced out and the dsRNA is supplied as a hairpin structure. When the dsRNA is expressed in a cell, as noted above, ribonucleases bind to and cleave the double-stranded RNA, thereby initiating the cascade of events leading to degradation of the target mRNA molecules, and thereby silencing target genes. The phenomenon of RNA interference is described in Bass, Nature 411: 428-29 (2001); Elbahir et al., Nature 411: 494-98 (2001); and Fire et al., Nature 391: 806-11 (1998); and WO 01/75164, where methods of making interfering RNA also are discussed.

For example, to reduce expression of a target gene in an insect pest using RNAi, an expression cassette encoding a double-stranded RNA having the sequence of an mRNA transcribed from the target gene, or a substantially identical sequence (including those engineered not to translate the protein), or fragment thereof, is introduced into a yeast cell. The resulting yeast cell can then be fed to the insect pest to determine its ability to inhibit expression of the target gene and/or inhibit growth of the insect pest.

The RNAi polynucleotide can hybridize with the full-length mRNA encoded by the target gene or hybridize to a fragment of the target RNA or DNA (the target sequence). The target sequence will typically be at least about 10, 15, 20, 50 or 100 nucleotides in length, but usually comprise less than about 500 nucleotides. Often, the target sequence and/or the dsRNA sequence is between about 50 and about 400 nucleotides in length, usually between about between 100 and about 300 nucleotides.

Although the sequence of the dsRNA used for RNAi need not be completely identical to the target sequence of the target gene, it is typically substantially identical, e.g., at least 70%, 80%, 90%, 95%, 98%, or more identical to the target sequence.

Target genes can be selected based any of a number of criteria. Such criteria include for example: gene essentiality, midgut expression level, degree of divergence from related species sequences, and target effectiveness demonstrated in previous studies. In the case of Drosophilids, suitable target genes include, for example, y-tubulin 23C. blw. Ace, RpL19 and acetylcholine esterase. Suitable target genes for *D. suzukii* can be identified in the Spotted Wing Flybase (see, spottedwingflybase.oregonstate.edu). Suitable RNAi targets for three insect species: *D. suzukii, Halyomorpha halys* (brown marmorated stink bug), and *Leptinotarsa decemlineata* (Colorado potato beetle) are provided in the sequence listing. Other suitable targets include B actin for Colorado potato beetle, V-ATPase for western corn rootworm, and hunchback for the pea aphid (*Acrythosiphon pisum*).

In addition to RNAi, other inhibitory RNA techniques are known. For instance, antisense technology can be conveniently used to inactivate gene expression. To accomplish this, a nucleic acid segment from the desired gene is cloned and operably linked to a promoter such that the antisense strand of RNA will be transcribed. The expression cassette is then introduced in the yeast cell and the antisense strand of RNA is produced (see e.g., Sheehy et al., *Proc. Nat. Acad Sci. USA,* 85:8805-8809 (1988); Pnueli et al., *The Plant Cell* 6:175-186 (1994); and Hiatt et al., U.S. Pat. No. 4,801,340).

Catalytic RNA molecules or ribozymes can also be used to inhibit expression of a target gene. Ribozymes that specifically pair with a target RNA and cleave the phosphodiester backbone at a specific location can be designed to functionally inactivating the target mRNA. In carrying out this cleavage, the ribozyme is not itself altered, and can cleave other molecules, making it a true enzyme. The inclusion of a ribozyme sequence in an antisense RNA confers RNA-cleaving activity, thereby increasing the activity of a given antisense construct. The design and use of target RNA-specific ribozymes is described in Haseloff et al. *Nature,* 334:585-591 (1988).

Another method of suppression is sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes (Napoli et al., *The Plant Cell* 2:279-289 (1990); Flavell, *Proc. Natl. Acad. Sci., USA* 91:3490-3496 (1994); Kooter and Mol, *Current Opin. Biol.* 4:166-171 (1993); and U.S. Pat. Nos. 5,034,323, 5,231,020, and 5,283,184).

Production of Transgenic Yeast Cells

Production of recombinant yeast cells is well known. Yeast species of interest in the present invention include *Saccharomyces cerevisiae, Pichia pastoris,* and *Hanseniaspora uvarum, H. uvarum* has been isolated as the most common yeast species in the gut of *D. suzukii* and is particularly useful for control of this species. Suitable promoters for expression in yeast are also well known and include, for example, the bacteriophage T7 promoter, promoters from GAL1 (which is induced by the presence of galactose), ADH1, the TEF1 promoter and the AOX promoter (an methanol inducible promoter) and the like. Many yeast cloning vectors have been designed and are readily available. Methods for transforming *S. cerevisiae* cells with exogenous DNA and producing recombinant products polypeptides are also well known. Transformed cells are selected by phenotype determined by a selectable marker, commonly drug resistance or the ability to grow in the absence of a particular nutrient (e.g., leucine).

In addition, in some embodiments, auxotrophic yeast strains are used. Use of these strains relies on marker genes that encode key enzymes in various essential metabolic pathways. Examples include the URA, HIS3, LEU2, TRP1, and MET15 marker genes which encode essential enzymes for de novo synthesis of pyrimidines, 1-histidine, 1-leucine, 1-tryptophan, and 1-methionine, respectively. Yeast strains are auxotrophic for the nutrient in question due to the absence of a functional chromosomal copy of the marker gene. The auxotrophic yeast strains can thus be propagated only in media that contain the appropriate nutrients.

Alternatively, synthetic auxotrophs can be engineered to require particular compounds. For example, bacteria have been engineered to be viable only in the presence of the synthetic molecule benzothiazole[39], which prevents genetically modified bacteria from escaping and increases biosafety. This technology could be applied to yeast biopesticides to prevent unwanted escapes.

Lure Traps

Lure traps are commonly used to attract and kill insect pests. Design and use of such traps are well known to those of skill in the art. A lure trap of the invention can be any device into which the recombinant yeast of the invention are placed, and that prevents the insect pest from escaping once the insect pest has come into contact with the trap. The traps can be of various sizes, shapes, colors, and materials. Traps of the present invention can be designed and manufactured specifically for use as an insect trap, or can be a container converted and adapted from other uses such as, for example, a glass Petri dish, a metal coffee can, a cardboard box, or any ordinary plastic, metal, fiberglass, composite or ceramic container.

Considerable research has been directed at determining the natural volatile compounds that attract vinegar flies to their hosts, and incorporating them into lures for commercial traps. For example, yeast have been incorporated into lure traps for vinegar flies (see e.g., U.S. Pat. No. 8,940,287). Such a trap may comprise yeast in combination with a growth medium (e.g., sugar and water). The growth medium can also include chemicals or nutrients necessary to induce expression of the dsRNA in transformed yeast cell. The trap may also comprise dried or fresh vegetable matter.

EXAMPLE

The following example is offered to illustrate, but not to limit the claimed invention.

Materials and Methods

Animal Models

For all insect bioassays, the researcher was blinded from the identity of the treatment during the course of the experiment. Insects were assigned to treatment groups by pooling same aged individuals from several rearing bottles and randomly redistributing into groups. A different generation of flies was used in each experimental replicate.

Fly Strains and Rearing

All *Drosophila* species and strains tested in our studies as well as their collection sites are Table 1. All lines were maintained in Fisherbrand square, polyethylene, 6 oz. stock bottles (Fisher Scientific. Pittsburgh, Pa.) containing 50 ml of Bloomington stock center *Drosophila* food recipe. Colonies were kept between 22° C. to 25° C. in a cabinet incubation chamber (Percival Scientific, Inc., Perry, Iowa) with a 12:12 h light:dark cycle.

TABLE 1

*Drosophila* strains

| Species | Strain | Location of collection |
|---|---|---|
| D. suzukii | Mixed Watsonville population | Watsonville, CA |
| D. biarmipies | genome strain, 361.0-isol e-11 | Ari Ksatr, Cambodia |
| D. melanogaster | Oregon R | Roseburg, Oregon |
| D. simulans | W501 | Genome Strain |

Target Gene Selection for Double Stranded RNA (dsRNA) Knockdown

Target genes were selected based on four main criteria: gene essentiality, midgut expression level, degree of divergence from related species sequences, and target effectiveness demonstrated in previous studies. We assumed that genes with essential functions in *D. melanogaster* would also have essential functions in *D. suzukii*. Genes with lethal null phenotypes recorded in Flybase.org were considered essential. We hypothesized that the dsRNA produced by the yeast would be absorbed by the midgut tissues in the fly, so we selected target genes that are expressed in the adult and larval midgut. Midgut expression was determined using the FlyAtlas database of microarray data [44]. Conservation of target sequences between species was also considered when selecting gene fragments. The *D. suzukii* y-tubulin 23C target sequence was designed to be highly divergent from members of the *melanogaster* subgroup by targeting the 3' untranslated region (UTR). The blw, Ace, and RpL19 target sequences were chosen from coding regions and are more conserved across species. Alignments of target gene sequences for *D. suzukii, D. biarmipes, D. melanogaster,* and *D. simulans* and identity scores (Table 2) were generated with ClustalW2 [45]. Previous studies have implicated tubulin as an effective RNAi target in coleopteran pests [32]. dsRNA targeting blw and RpL19 caused increased cell death in *D. melanogaster* tissue culture experiments [46], so we selected homologous target gene fragments from *D. suzukii* sequences. Chemical pesticides commonly disrupt neurotransmission by inhibiting the function of acetylcholine esterase, so we chose to target this gene as well. Target gene fragment sequences are listed in the sequence listing. Spotted Wing Flybase accession numbers were used as identifiers and sequences can be retrieved from Spotted Wing Flybase (see, spottedwingflybase.oregonstate.edu).

TABLE 2

Sequence conservation of target gene fragments

| gene | species | identity | longest match | NCBI accession |
|---|---|---|---|---|
| bellwether | D. biarmipies | 99% | 130 bp | KB462602 |
| bellwether | D. melanogaster | 96% | 42 bp | NM_166554 |
| bellwether | D. simulans | 95% | 50 bp | CM002911 JPYS01000000 |
| y-tubulin 23C | D. biarmipies | 90% | 47 bp | KB462641 AFFD02000000 |
| y-tubulin 23C | D. melanogaster | 76% | 15 bp | NM_057456 |
| y-tubulin 23C | D. simulans | 74% | 16 bp | XM_002077929 CM002910 |

Construction of Vectors for In Vitro Synthesis of dsRNA

1 µg of *D. suzukii* total RNA was used to synthesize cDNA using ThermoScript RT-PCR System (Life Technologies, Grand Island, N.Y.) according to the manufacturer's protocol. Target gene fragments y-tubulin 23C and Vacuolar H+-ATPase 26 kD subunit were PCR amplified from *D. suzukii* total cDNA using AccuPrime Taq DNA Polymerase (Life Technologies, Grand Island, N.Y.) following manufacturer's specifications and ligated into pCR2.1 using The TA Cloning Kit (Life Technologies, Grand Island, N.Y.). The primer sequences used for molecular cloning are listed in Table 3. The T7 promoter sequence (5'-TAATACGACT-CACTATAGG-3') was added to the 5' end of the forward and reverse primer sequences.

In Vitro RNA Synthesis

Target gene fragments y-tubulin 23C and vacuolar H+-ATPase 26 kD subunit were PCR amplified from pCR2.1 vectors containing the target sequences and convergent T7 promoters. PCR products were purified with the QiaQuick PCR Purification Kit (Qiagen, Valencia, Calif.). Purified PCR product was used as template for in vitro transcription using the MEGAscript T7 Transcription Kit (Life Technologies, Grand Island, N.Y.) following manufacturer's instructions.

Construction of Plasmid Vectors for Expression of dsRNA in Yeast

Yeast expression vectors containing inverted repeats of ~200 bp *D. suzukii* target gene sequence joined by a 74 bp intron sequence from the *D. melanogaster* white gene were constructed in two cloning steps. The intron and the target sequence were inserted in the forward orientation in the first step, and the target sequence was inserted in the reversed orientation in the second step. Target gene fragments y-tubulin 23C, bellwether, acetylcholine esterase, and ribosomal protein L19 were PCR amplified from *D. suzukii* total cDNA using AccuPrime Taq DNA Polymerase (Life Technologies, Grand Island, N.Y.) following manufacturer's specifications. A BamHI restriction site was added to the 5' end of the forward primer sequence, and a EcoRI restriction site was added to the 5' end of the reverse primer sequence (see Table 3 for primer sequences). The second intron of the white gene was PCR amplified from *D. melanogaster* total cDNA using primers with a BamHI restriction site added to the 5' end of the forward and a EcoRI site added to 5' end of the reverse primer. PCR products were purified with the QiaQuick PCR Purification Kit (Qiagen, Valencia, Calif.) and target sequences were digested with restriction enzymes BamHI and XbaI, and the white intron was digested with BamHI and EcoRI (New England Biolabs, Ipswitch, Mass.). The *S. cerevisiae* expression vector p406TEF1 (Addgene, Cambridge, Mass.) was digested with XbaI and EcoRI. Digested PCR products and vector DNA were purified with gel electrophoresis and the QiaQuick Gel extraction kit following manufacturer's instructions. The vector, target sequence, and intron were ligated together with T4 DNA ligase (New England Biolabs, Ipswitch, Mass.). Ligation products were transformed into *E. coli* and plasmid DNA was extracted from the clones. Sequencing was performed to confirm presence of the forward target sequence and the intron. Target gene fragments were amplified from the confirmed DNA clones using a reverse primer with EcoRI on the 5' end and a forward primer with HindIII on the 5' end. Confirmed DNA clones were restriction digested with EcoRI and HindIII. Digested PCR products and DNA vectors were gel purified and ligated together with T4 DNA ligase. The complementary sequences in the completed vectors created secondary structure that prevented Sanger sequencing, so completed clones were restriction digested with XbaI and EcoRI, or BamHI and HindIII, and gel purified digestion products were used for sequencing for confirmation of successful expression vector construction.

Transformation of Plasmids into *S. cerevisiae*

DNA vector p406TEF1 containing inverted repeats of *D. suzukii* target gene sequence were transformed into *S. cerevisiae* strain INVSc1 (Life Technologies, Grand Island, N.Y.) using the Frozen EZ Yeast Transformation kit II (Zymo, Irvine, Calif.) following manufacturer's instructions. Transformants were selected on minimal media without uracil and confirmed by colony PCR. PCR reactions were performed as described above with a forward primer located upstream of the multiple cloning site and the reverse primer located within the white intron.

Isolation of RNA from Yeast 1.5 mL liquid yeast culture was pelleted at 12,000 rpm for 1 minute. 300 µl of TRI-reagent (Sigma Aldrich, St Louis, Mo.) was added to the pellet and homogenized by vortexing with 100 µl acid-washed 425-600 µm glass beads (Sigma Aldrich, St Louis, Mo.). One-fifth volume of 100% chloroform was added to each sample and incubated at room temperature for 10 minutes. Samples were spun down at 13,000 rpm for 15 m 390 minutes at 4° C. The upper aqueous layer was collected and nucleic acid was precipitated by adding an equal volume of 100% isopropanol and incubated at room temperature for 10 minutes. Samples were spun down at 13,000 rpm for 15 minutes at 4° C., and pellets were washed once with two volumes of 70% ethanol. Pellets were resuspended in 20 µl 1× Turbo DNase buffer (Life Technologies, Grand Island, N.Y.) and treated with 1 ul Turbo DNase following manufacturer's instruction. RNA concentrations were quantified with a NanoDrop 2000 Spectrophotometer (Fisher Scientific, Pittsburgh, Pa.).

Treatment of Larvae with In Vitro Transcribed dsRNA

2nd instar larvae were separated from fly food and rinsed with water. 100 µl of a solution containing 1 mg/ml in vitro transcribed dsRNA, 3% Lipofectamine 2000 (Life Technologies, Grand Island, N.Y.), and Schneider's *Drosophila* medium (Life Technologies, Grand Island, N.Y.) was pipetted onto a plastic dish forming a droplet. 10 larvae were gently added to each droplet and soaked for 1 hour. Larvae were returned to a small dish of fly food and mortality was assessed 24 hours later and at the time of eclosion, or larvae were collected for RNA isolation at the same time-point when mortality was assessed.

Yeast Feeding Assay for Adults and Larvae

Yeast colonies expressing dsRNA were incubated in 4 ml minimal media without uracil at 30° C., and 225 rpm for 24 hours. 4 ml cultures were used to inoculate 300 ml cultures and incubated at 30° C. for 24 hours. Liquid culture was pelleted at 5,000 rpm for 15 minutes. To feed larvae, pelleted yeast was mixed with standard Bloomington *Drosophila* fly food medium at a ratio of 1:1 by weight and fed to larvae in 12-well tissue culture plates. After yeast feeding period, larvae were transferred to a vial containing standard Bloomington *Drosophila* medium to grow to adulthood, or were collected for RNA isolation. To feed adults, pelleted yeast was spread thinly on a wooden tongue depressor coated in YPD agar (Sigma Aldrich, St Louis, Mo.). The yeast-covered tongue depressor was imbedded upright in a vial containing standard Bloomington *Drosophila* medium and 30 adult flies were added to each vial. To confirm the adults and larvae ingest the yeast, red food coloring was added to the liquid yeast culture (McCormick), and midguts were dissected and inspected visually under a light microscope.

Activity Monitoring

Male adult flies were loaded individually into glass tubes for activity monitoring using *Drosophila* Activity Monitoring System (DAMS) (Trikinetics, Waltham, Mass.) following three days of yeast feeding treatment. The glass tubes were filled at one end with media containing 5% agar and 2% sucrose by weight. Percival incubators were set to 25° C. with a photoperiod of 12 hours of light and 12 hours of dark. Fly activity monitoring using DAMS and data analysis using FaasX were as previously described 47427

Assessment of Fecundity and Viability of Offspring

Standard Bloomington *Drosophila* medium was dyed green with food coloring (McCormick) to provide visual contrast to eggs. 1 ml hot media was pipetted onto a small plastic spoon and allowed to cool. Once solidified, media was painted with a thin layer of wild type *S. cerevisiae* grown in liquid culture to encourage oviposition. Spoons were placed inside empty fly vials (Genesee Scientific, San Diego, Calif.) and one male and one female were added to the vial. After the egg-laying period, eggs were counted visually under a stereomicroscope. The spoon was transferred to a vial containing *Drosophila* medium and eggs were allowed to grow to adulthood.

Isolation of RNA from Adult and Larval Midgut

Following yeast feeding treatment, live adults were anesthetized with carbon dioxide and live larvae were separated from yeast mixture. Adults and larvae were transferred to a microcentrifuge tube containing TRI-reagent (Sigma Aldrich, St Louis, Mo.) and kept on ice. Dissection of the midgut was performed immediately on ice in chilled RNAlater (Life Technologies, Grand Island, N.Y.). Midguts were washed 2× in chilled nuclease-free water and 300 µl TRI-reagent was added to the microcentrifuge tube. Midguts were homogenized by grinding using a motorized pestle and RNA isolation was performed as described above in yeast RNA isolation.

Quantitative Real-Time PCR (qRT-PCR)

1 µg of total RNA was used to synthesize cDNA using ThermoScript RT-PCR System (Life Technologies, Grand Island, N.Y.) according to the manufacturer's protocol. Dilutions (1:10) of cDNA samples were used in qRT-PCR reactions. Gene-specific primers were designed based on sequence analysis using the *D. suzukii* genome scaffold and optimized at an annealing temperature of 63.3° C. Melt curve and BLAST analysis were used as criteria to determine primer specificity. The qRT-PCR assays were performed using SsoAdvanced SYBR Green Supermix (Bio-rad, Hercules, Calif.) in a CFX96 Touch Real-Time PCR Detection thermal cycler (Bio-Rad, Hercules, Calif.). Cycling conditions were 95° C. for 30 seconds, 40 cycles of 95° C. for 5 seconds, followed by an annealing/extension phase at 63.3° C. or 55° C. for 30 seconds. The reaction was concluded with a melt curve analysis going from 65° C. to 95° C. in 0.5° C. increments at five seconds per step. Three technical replicates were performed for each data point of each biological replicate, and at least 4 biological replicates were performed for analysis of each gene. Data were analyzed using the standard ΔΔCt method and target gene mRNA expression levels were normalized to the reference gene Cbp20 mRNA levels. Finally, average relative expression values for treated samples were divided by the average control values to represent the fold change of target gene expression in the treated sample.

Results

Figure 1:
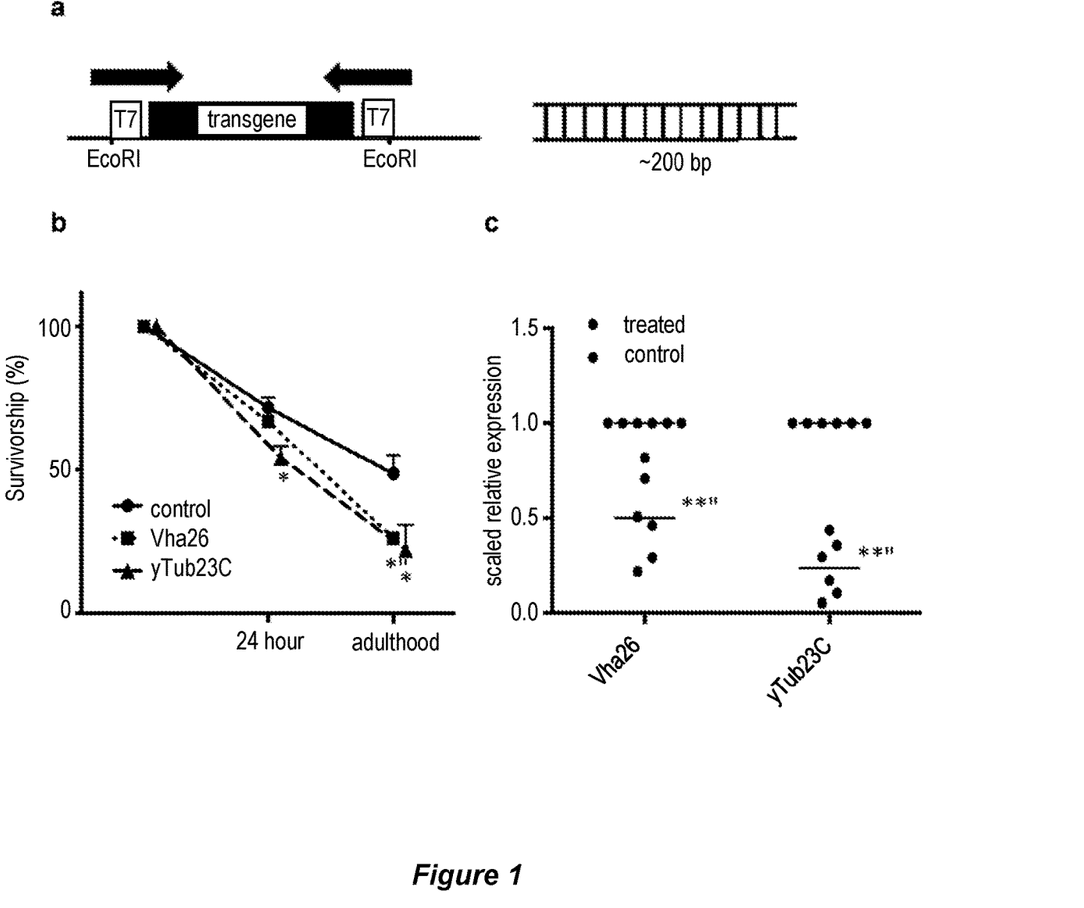
FIGS. 1a to 1c show that D. suzukii larvae treated with in vitro transcribed dsRNA have increased mortality and decreased target gene expression. (a) Map of vector for in vitro transcription of dsRNA using convergent T7 promoters flanking ~200 bp of D. suzukii target gene sequence. Black arrows indicate direction of transcription. (b) Survivorship of 2nd instar larvae following soaking treatment with dsRNA solution. Mortality was assessed 24 hours after treatment and at the time of eclosion. A total of 160 larvae were tested in each treatment, and data represent mean and s.e.m. of three independent experiments. (c) Suppression of target genes yTub23C and Vha26 in whole larvae 24 hours after treatment with dsRNA solution. Ten larvae were homogenized to obtain one RNA sample. Expression was quantified with RT-qPCR and normalized against housekeeping gene Cbp20. Each data point represents a biological replicate, and horizontal lines indicate the mean. (b) and (c) Asterisks represent significance as determined by two-tailed t-test (* indicates $p<0.05$, and ** indicates $p<0.01$).
Figure 2:
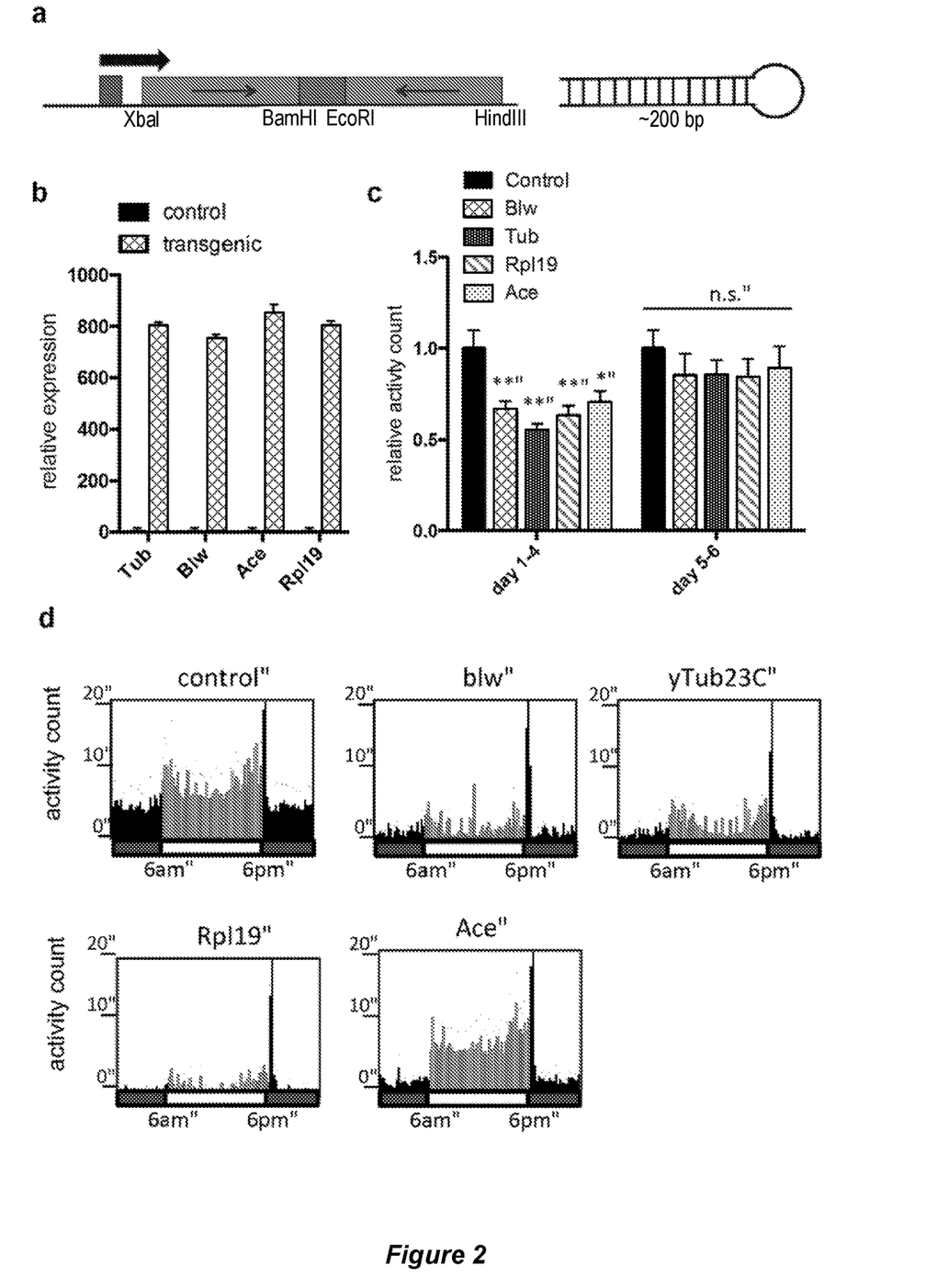
FIGS. 2a to 2d show that D. suzukii adults fed on yeast expressing dsRNA have decreased locomotor activity levels. (a) Map of transformation vector for expression of hairpin dsRNA in S. cerevisiae. ~200 bp of D. suzukii target gene sequence was inserted into p406TEF1 to form inverted repeats linked by 74 bp of intron sequence from the white gene. Black arrow indicates direction of transcription. (b) Expression of dsRNA in S. cerevisiae. Expression was quantified with RT-qPCR and was normalized against housekeeping gene actin. Data represent mean and s.e.m. of three technical replicates. (c) Locomotor activity levels in D. suzukii following a three day treatment with yeast expressing dsRNA targeting D. suzukii blw, yTub23C, Ace, and RpL19. Male adult flies were fed ad libitum with a choice between artificial diet and live yeast for three days. Activity was recorded for 6 days after the feeding period using the DAMS. The first through the fourth days of recording were averaged together, and days 5 and 6 were averaged. Data represent mean and s.e.m. of 3 independent experiments, and a total of 96 flies were tested per treatment. Each experiment was normalized to the average of the control treatment. One-way ANOVA was performed ($p=0.0009$) and significance relative to the control was determined by post hoc Bonferroni corrected t-test (* indicates $p<0.05$ and ** indicates $p<0.01$). (d) Activity levels plotted over the second day of recording following three days of feeding treatment. Each bar represents average activity counts in 15-minute increments. Black bars indicate lights off and grey bars represent lights on. Each eduction graph represents an average of 32 flies in one experiment. Representative eduction graphs are shown here.

Treatment of Larvae with In Vitro Transcribed dsRNA Reduces Expression of Target Genes and Decreases Survival to Adulthood Previous studies have demonstrated dsRNA can be synthesized and fed to insects in solution or artificial diet, resulting in gene knockdown and mortality [1,29-31]. This method is often used to select targets for in vivo testing. Critical genes tubulin and vacuolar ATPase are commonly used target genes and have effectively induced mortality in coleopterans [32]. First, we examined whether dsRNA targeting y-tubulin 23C (yTub23C) and vacuolar H+ ATPase 26 kD subunit (Vha26) could be used to induce mortality in D. suzukii larvae. dsRNA was transcribed in vitro using a plasmid containing approximately 200 bp D. suzukii target gene sequence flanked with convergent T7 promoters (FIG. 1a). We found that a one-hour soaking treatment with in vitro transcribed dsRNA reduced survival to adulthood by 54% and 46% respectively (FIG. 1b). Next, we asked if the increased mortality was due to changes in target gene expression level. RNA was extracted from whole larval bodies 24 hours after the one-hour soaking treatment. Target transcripts yTub23C and Vha26 were reduced by 76% and 50% respectively in treated samples (FIG. 1c). These results suggest dsRNA in the soaking solution is absorbed and able to trigger an RNAi response in the larvae, resulting in mortality.

dsRNA Targeting Critical D. suzukii Genes is Expressed in Modified Saccharomyces cerevisiae DNA plasmids were constructed to constitutively express dsRNA hairpins targeting D. suzukii critical genes. Approximately 200 bp D. suzukii target gene sequence was inserted into a DNA plasmid to formed inverted repeats joined by 74 bp of intron sequence from the white gene from D. melanogaster (FIG. 2a). This plasmid is self-replicating and does not integrate into the host genome, so the host genome remains unchanged. Plasmids were transformed into S. cerevisiae strain INVSc1 using heat shock and expression of dsRNA was verified using RT-qPCR (FIG. 2b). Empty P406TEF1 plasmid was transformed to use as a control strain. As a control for dsRNA treatments, some studies use dsRNA targeting a gene from another species, such as GFP. We chose to use a yeast that contains empty plasmid and expresses no dsRNA as the control strain to avoid possible off target effects, such as suppression of critical genes that may have regions of sufficient homology to the control sequence to bring about an RNAi response [33].

D. suzukii Adults Fed on Yeast Expressing dsRNA have Decreased Locomotor Activity Levels Adult D. suzukii males were fed ad libitum for three days with a choice between standard Drosophila artificial diet and live yeast growing on solid agar. To verify that the flies consumed the yeast, yeast were grown with red food coloring and midguts were dissected and examined after feeding. When fed on live yeast expressing dsRNA targeting bellwether (blw), Ribosomal protein L19 (RpL19), acetylcholine esterase (Ace), and yTub23C, adult D. suzukii had decreased locomotor activity in the 4 days following treatment (FIG. 2c). The rationale for selection of these target genes is stated in the methods section. Although activity levels were reduced in flies treated with dsRNA, flies in all treatments maintained typical temporal patterns of activity through the day (i.e. anticipation of dawn and dusk, and peak of activity at dusk) (FIG. 2d). We found this effect on locomotor activity level persisted over the first four days following the feeding period, but the activity levels of the treated flies were not significantly different from the control flies by the fifth or sixth day following the feeding period (FIG. 2c). This result indicates the treated flies were able to recover from the dsRNA treatment.

Figure 3:
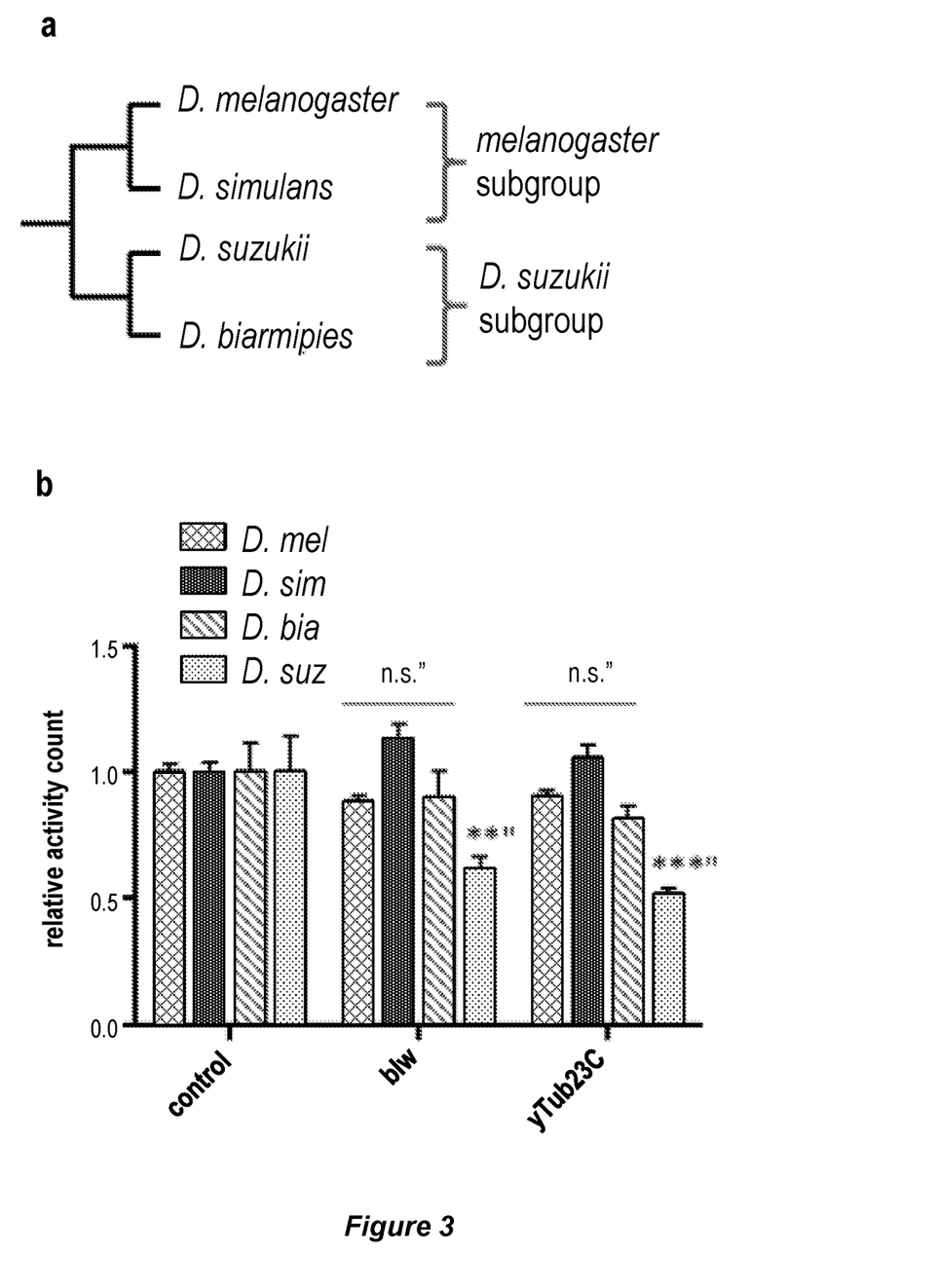
FIGS. 3a to 3c show that the effects of yeast feeding treatment on adult activity levels are species specific. (a) Cladogram of melanogaster and suzukii subgroups. Only the tested species were included in the cladogram. (b) Relative locomotor activity levels in D. suzukii, D. melanogaster, D. simulans, and D. biarmipes following a three-day treatment with yeast expressing dsRNA against bellwether and yTub23C. Activity was recorded using the DAMS during the 4 days following the treatment. Data represent averages and s.e.m. of 3 independent experiments, and a total of 96 flies were tested per treatment. Each replicate was normalized to the average of the control treatment. Two-way ANOVA was performed ($p=0.0001$) and significance relative to the control was determined by post hoc Bonferroni corrected t-test ( indicates $p<0.01$, and * indicates $p<0.001$). (c) Activity levels plotted over the second day of recording following three days of feeding treatment. Each bar represents average activity counts in 15-minute increments. Black bars indicate lights off and grey bars indicate lights on. Each eduction graph represents an average of 32 flies in one experiment. Representative eduction graphs are shown here.

The Effects of Yeast Feeding Treatment on Adult Locomotor Activity Levels are Species Specific The benefit of using RNAi in pest management is that RNAi triggers can be designed to target pest species, but not beneficial insects. To demonstrate this, we fed yeast expressing dsRNA to other Drosophilids and found that even closely related species were unaffected by the treatment (FIG. 3b), D. biarmipes is closely related to D. suzukii, while D. melanogaster and D. simulans and more distant relatives (FIG. 3a), D. simulans, D. biarmipes, and D. melanogaster were unaffected by treatment with yeast expressing dsRNA targeting blw and yTub23C. All species maintained regular temporal patterns of activity throughout the day (FIG. 3c). Homologous gene target gene fragments were identified for each species by BLAST sequence alignment [34], and sequence identity scores were calculated (Table 1). The blw target gene fragment was designed to be highly conserved, with 95% to 99% conservation between D. suzukii and the other Drosophila species. Surprisingly, closely related D. biarmipes did not have significantly reduced activity, despite 130 consecutive matching base pairs in the target gene fragment, D. melanogaster and D. simulans have 42 and 50 consecutive matching base pairs to the blw fragment, respectively. The yTub23C target gene fragment was designed to be divergent by targeting the 3' untranslated region and is 90% to 74% conserved. We predicted the yTub23C fragment would be less effective on species other than D. suzukii due to reduced base pair matching. The lack of an effect on activity in species other than D. suzukii suggests that a high degree of perfect base pair matching is required to reduce locomotor activity. These results imply the mechanism responsible for this reduction in activity level is target sequence dependent. Alternatively, it is possible that blw is sufficiently conserved in other species to be susceptible to RNAi, but there are different regulatory mechanisms in other species that can better compensate for the knockdown of this critical gene. Another alternative explanation for the differences in activity level between species following treatment could be that the dosage varies by species, since the feeding assay was conducted ad libitum.

Figure 4:
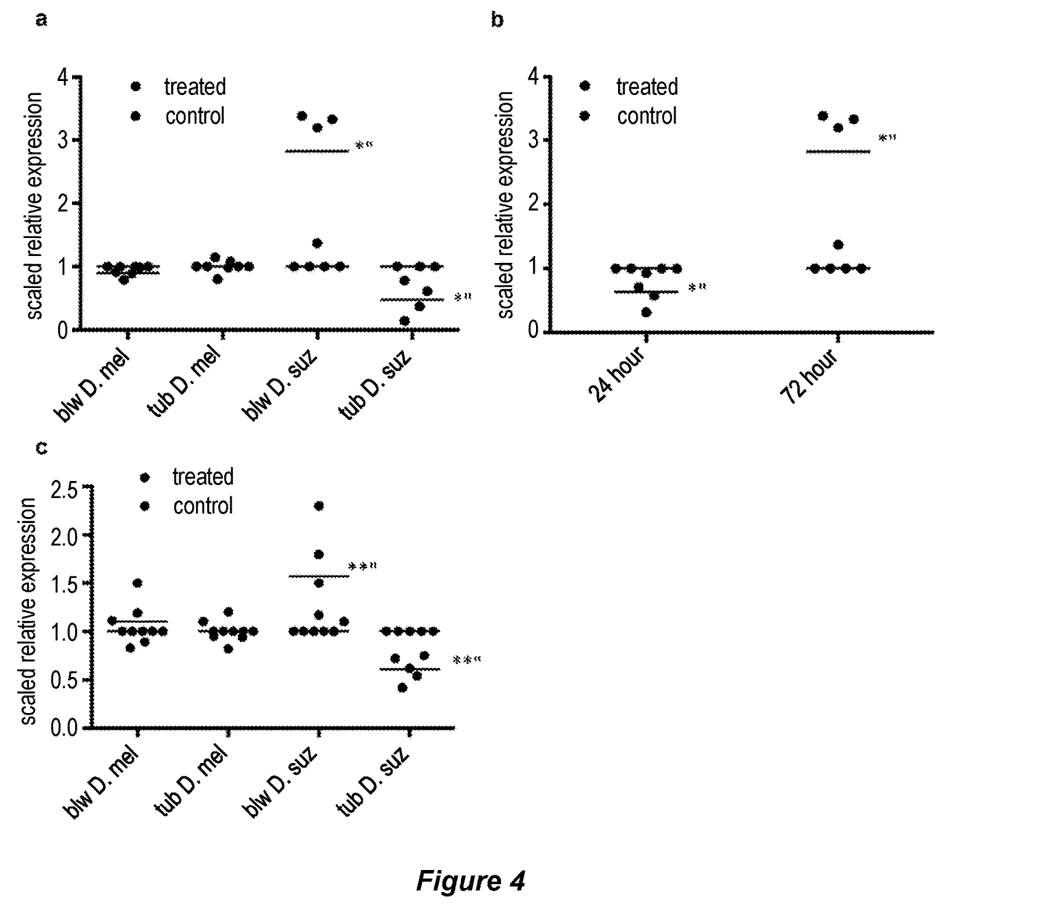
FIGS. 4a to 4c show that altered target gene expression in midgut following yeast feeding treatment. Relative expression of target genes bellwether and y-tubulin 23C in (a) adult midgut and (c) larval midgut following three days of treatment with yeast expressing dsRNA. (b) Relative expression in larval midgut of target gene blw following 24 and 72 hours of treatment with yeast expressing dsRNA. Ten midguts were dissected and homogenized to obtain one RNA sample. Expression was quantified with RT-qPCR and was normalized against housekeeping gene CBP20. The expression level in the control is scaled to one and treated expression levels are plotted relative to the control. Each data point represents one biological replicate and the horizontal line indicates the mean. For (a) and (b) n=4, and (c) n=5. Two-way ANOVA was performed and significance relative to the control was determined by post hoc Bonferroni corrected t-test (* indicates p<0.05, and ** indicates p<0.01).

Ingestion of Yeast Biopesticide Alters Expression Level of Target Genes with Species Specificity RNAi is not systemic in Drosophila, meaning RNAi only occurs within cells that contain dsRNA 35. The midgut is the only portion of the alimentary tract that is not keratinized and is thought to be the main site of dsRNA absorption, so we examined the midgut tissues post treatment to measure changes in target gene expression in adults and larvae, D. suzukii larvae fed on yeast expressing dsRNA targeting yTub23C for 72 hours had reduced yTub23C mRNA levels in the midgut, and larvae fed on yeast targeting blw had significantly increased expression of blw (FIG. 4a). Although RNAi directly reduces target transcript levels through cleavage and degradation, previous studies have demonstrated that compensatory mechanisms can cause upregulation of target genes following an RNAi response[36]. To determine if this was the case, we measured blw expression after 24 hours of treatment with yeast targeting blw and found that expression is decreased after 24 hours (FIG. 4b). This result suggests knockdown of blw is occurring soon after initial yeast exposure, and over several days, a compensatory mechanism causes increased expression of the target gene. Adult D. suzukii midgut gene expression following yeast treatment was similar to the results in larvae, i.e. blw expression was elevated following treatment, and γTub23C was decreased (FIG. 4c). We did not find significant changes in target gene expression in D. melanogaster larva or adult midguts following 72 hour yeast feeding treatments (FIG. 4a, 4b). The lack of change in target gene expression in D. melanogaster was not surprising, since we also saw no changes in locomotor activity. These observed changes in target gene expression in D. suzukii but not D. melanogaster indicate precise target gene sequence matching is required to elicit an RNAi response. Moreover, larvae were subjected to a no-choice feeding assay, so differences in gene expression between D. suzukii and D. melanogaster larvae are not dependent on dosage.

Ingestion of Yeast Biopesticide Reduces Reproductive Fitness.

Figure 5:
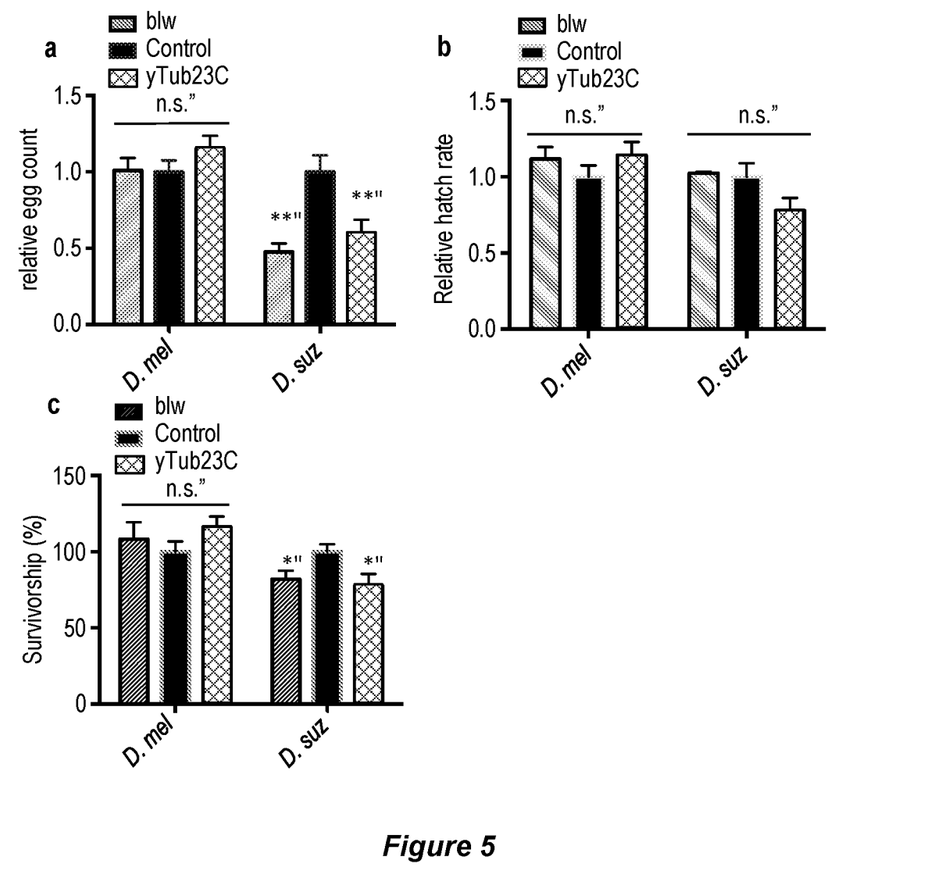
FIGS. 5a to 5c show that yeast feeding treatment of adults and larvae decreases larval survivorship and adult reproductive fitness with species specificity. (a) Relative egg counts of D. melanogaster and D. suzukii. Virgin females and males were fed separately on yeast expressing dsRNA against blw and yTub23C for three days. One male and one female were crossed and allowed to lay eggs for 48 hours (D. melanogaster) or 72 hours (D. suzukii). (b) Relative hatch rate of D. melanogaster and D. suzukii eggs when parents were fed as described in (a). The hatch rate was determined by dividing the number of adults by the number of eggs recorded in that vial. Data shown in (a) and (b) represent mean and s.e.m. of three independent experiments and a total of 75 females were tested per treatment. Each replicate was normalized to the mean of the control. Two-way ANOVA was performed and significance relative to the control was determined by post hoc Bonferroni corrected t-test (** indicates p<0.01). (c) Survivorship of D. melanogaster and D. suzukii 2nd instar larvae following 24 hour treatment with live yeast expressing dsRNA against blw and yTub23C. Larvae were fed on a mixture containing 50% artificial diet and 50% live-pelleted yeast by volume. Mortality was assessed at the time of eclosion. Data shown in (c) represent mean and s.e.m. of six independent experiments and a total of 300 larvae were tested per treatment. Each replicate was normalized to the mean of the control and significance relative to the control was determined by a two-tailed t-test (* indicates p<0.05).

Decreased reproductive fitness of an insect pest can reduce the population size within a region, minimizing crop losses. To test if the yeast treatment affects reproductive fitness, we counted the number of eggs deposited per female post-treatment and measured the survival rate of the offspring. We found that yeast expressing dsRNA that targets blw and γTub23C caused significant decrease in the number of eggs laid by D. suzukii, but not by D. melanogaster (FIG. 5a). One explanation of this result is that induction of RNAi reduces overall fitness, so females are unable to devote resources towards producing eggs. An alternative explanation is that because treated flies are less active, the first mating is delayed compared to the control, resulting in fewer eggs at the end of the test period. The survival rates of the offspring of treated adults as measured by egg hatch rate were unaffected in both species (FIG. 5b). In our assay, the food source was coated with wild type yeast to encourage oviposition, which may have interfered with passage of transgenic yeast from the parents to the offspring.

Ingestion of Yeast Biopesticide Decreases Larval Survivorship

Ingestion of yeast expressing dsRNA targeting blw and γTub23C during the larval stages decreased survival to adulthood in D. suzukii, but not in D. melanogaster (FIG. 5c). Adults of all tested species fed on yeast expressing dsRNA did not have increased mortality in this study. Larvae consume a greater amount of food per day compared to adults. Since the larvae were fed in a no-choice assay, and the adults were fed with a choice between live yeast and artificial diet, we reason that larvae likely received higher dosage of yeast. Differences in dosage could explain why the yeast feeding treatment induces mortality in larvae, but not in adults. Alternatively, we speculate larval stages could be more susceptible to RNAi than adults due to differences in the absorptive properties of the midgut or robustness of the RNAi pathway.

Discussion

Here we show that genetically modified yeast can be used to deliver dsRNA to an insect pest, causing decreased fitness through RNAi. Ingestion of this modified yeast by adult D. suzukii results in decreased locomotor activity and reduced egg laying. Larvae exhibit reduced survival to adulthood when fed on yeast expressing dsRNA, and adults and larvae have altered target gene expression following yeast feeding treatment. We find the effects of the yeast feeding treatment on fitness are species-specific, even when testing closely related species. Since species with divergent target gene sequences, such as D. simulans, were unaffected by the yeast feeding treatment, we find it unlikely that sequence-independent effects were responsible for the observed decreases in fitness. Changes in target gene expression following yeast feeding treatment were observed in D. suzukii but not in D. melanogaster (FIG. 4a), D. biarmipies, D. melanogaster, and D. simulans exhibited no changes in locomotor activity (FIG. 3b). Together, these results indicate sequence-dependent target gene knockdown via RNAi was the primary cause of decreased fitness observed in D. suzukii.

This yeast biopesticide could be improved as a delivery vehicle by additional modifications to the yeast genome. S. cerevisiae lacks a functional RNAi mechanism[37], which might make it a suitable dsRNA delivery vehicle if the absence of RNAi machinery promotes stability of dsRNA. On the other hand, the delivery of dsRNA pre-processed by DICER or other components of the RNAi machinery might induce a stronger RNAi response in insect cells compared to long, unprocessed dsRNA. Thus, the insertion of key dsRNA processing genes into the yeast genome should improve efficacy of this yeast biopesticide. Another improvement to the current design is to create modifications such that dsRNA is excreted from the yeast cells in membrane-bound vesicles. In the current design, dsRNA is expressed from circular DNA plasmids and remains within the cell. We hypothesize that dsRNA is absorbed into insect cells only when yeast cells are lysed within the insect midgut. It has been previously demonstrated that lipid encapsulated siRNA is more stable and more readily absorbed than naked siRNA[38]. Therefore, continuous excretion of dsRNA in membrane bound-vesicles from intact yeast should increase the dosage and absorption of dsRNA into insect cells.

The biosafety of this yeast biopesticide could be increased by adding a built-in mechanism of containment. A common concern with genetically modified organisms is their containment and potential negative impact on the environment. Yeast can be carried from one location to another by Drosophila, so it seems likely that genetically modified yeast could be spread beyond the boundaries of agriculture. Our design can be improved simply by placing the dsRNA under a promoter that requires the presence of an artificial molecule in order to prevent expression of dsRNA in the yeast where it is not wanted. Recently, bacteria known as synthetic auxotrophs were engineered to only be viable in the presence of the synthetic molecule benzothiazole[39], which prevents genetically modified bacteria from escaping and increases biosafety. This technology could be applied to yeast biopesticides to prevent unwanted escapes.

We predict that this yeast biopesticide could be successfully implemented in the field to combat D. suzukii. The emergence of insecticide resistance and increasing popularity of organic food products may open the door to non-chemical means of pest control in both organic and conventional farming. A method for administering this yeast biopesticide in the field has already been presented, since yeast baited traps have previously been used in berry crops to lure D. suzukii[27]. Additionally, there is precedence for the agricultural use of genetically modified fungi, as the USDA has issued 26 permits for environmental release of genetically modified fungi since 1995[40]. A major limitation of the current design is that mortality is not induced in adults. However, we found this yeast biopesticide significantly decreases egg laying and therefore could decrease the population size of the next generation. This yeast biopesticide could be used in complement with chemical pesticides by targeting detoxification genes rather than critical genes. By altering expression of detoxification genes, D. suzukii could be made more susceptible to chemical pesticides. As different types of insecticide resistance emerge, the genes targeted by the yeast could easily and quickly be changed to compensate. Targeting multiple genes simultaneously may also increase toxicity of this biopesticide. Further screening is required to identify groups of target genes that will have additive effects when knocked down together.

Another characteristic of yeast that makes it an interesting candidate for a biopesticide is that unlike chemical pesticides, it can be easily grown with commonplace starting materials. Currently, live *S. cerevisiae*, commonly known as brewer's yeast, can be purchased in packets from any grocery store. The yeast in these packets is dry and does not require refrigeration. We envision that in the future, a yeast biopesticide could be similarly packaged and distributed to farmers in developing countries, where it could be cultured at the site of use.

A limitation of all RNAi-based technology is potential off-target effects. Only partial complementarity between the guide strand and the endogenous mRNA is required to prevent translation, so silencing of related transcripts in humans and other non-target species is a concern. In addition to sequence-dependent off-target effects, introduction of dsRNA into mammalian cells can have sequence-independent effects on the immune system [41]. For example, dsRNA can activate an innate immune response in mammals, resulting in increased levels of inflammatory cytokines such as tumor necrosis factor and interferons [42]. In this pathway, dsRNA binds and activates protein kinase R, which phosphorylates and deactivates eukaryotic initiation factor eIF2, thereby inhibiting translation in cells that contain dsRNA [43]. Since these effects on the immune system are not dependent on the sequence of the dsRNA, even careful selection of target sequences cannot mitigate these off-target effects. Pesticides containing dsRNA will need further testing to determine if they are safe for human consumption.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

TABLE 3

Primers for molecular cloning and Quantitative PCR

| Purpose | Primer Name | Species | C ° | Sequence |
|---|---|---|---|---|
| qPCR | CBP20 F | *D. suzukii* | 63.3 | AGGAGCAGATCCACGAGCTC |
| qPCR | CBP20 R | *D. suzukii* | 63.3 | ACTCCACGAAGCAGAAGCC |
| qPCR | Tubulin F | *D. suzukii* | 63.3 | AATGTTTACCTATCCAAGCATG |
| qPCR | Tubulin R | *D. suzukii* | 63.3 | TCGAGTGGCAGAGTATGAATC |
| qPCR | Bellwether F | *D. suzukii* | 63.3 | TCATCTCGATTACCGATGGAC |
| qPCR | Bellwether R | *D. suzukii* | 63.3 | AACTCCAGCTTCATGGAACC |
| qPCR | Actin F | *S. cerivisiae* | 63.3 | ATTATATGTTTAGAGGTTGCTGCTTTGG |
| qPCR | Actin R | *S. cerivisiae* | 63.3 | CAATTCGTTGTAGAAGGTATGATGCC |
| qPCR | Blw dsRNA F | dsRNA detection | 63.3 | AGGCTGTGGCCTACCGTCA |
| qPCR | Blw dsRNA R | dsRNA detection | 63.3 | AGGGAGCCACCTCCCATG |
| qPCR | Tub dsRNA F | dsRNA detection | 63.3 | ACGGACGGTCAGGTACTAGC |
| qPCR | Tub dsRNA R | dsRNA detection | 63.3 | TGCGAGTCTTATAAACAATGTGCT |
| qPCR | Ace dsRNA F | dsRNA detection | 63.3 | TGAACAACATTTTCGGCAAG |
| qPCR | Ace dsRNA R | dsRNA detection | 63.3 | TGGGCATACTCGTTGGTG |
| qPCR | Rpl19 dsRNA F | dsRNA detection | 63.3 | TACCGTGTGCGCAAGAAC |
| qPCR | RpL19 dsRNA R | dsRNA detection | 63.3 | TGTCGATCTTCTTGCTGTCG |
| qPCR | CBP20 F | *D. melanogaster* | 55 | GTCTGATTCGTGTGGACTGG |

TABLE 3-continued Primers for molecular cloning and Quantitative PCR

| Purpose | Primer Name | Species | C° | Sequence |
|---|---|---|---|---|
| qPCR | CBP20 R | D. melanogaster | 55 | CAACAGTTTGCCATAACCCC |
| qPCR | Bellwether F | D. melanogaster | 55 | TCATCTCGATTACCGACGGAC |
| qPCR | Bellwether R | D. melanogaster | 55 | AACTCCAGCTTCATGGAACC |
| qPCR | Tubulin F | D. melanogaster | 55 | TTTCCCAATCAGGACGAGATC |
| qPCR | Tubuiln R | D. melanogaster | 55 | TGTTGATCTGCGAAAAGCTG |
| cloning | Ace(XbaI)F | D. suzukii | | GTGT TCTAGA TGCCACGGGACAAATATCTC |
| cloning | Ace(HindIII)F | D. suzukii | | GTGT AAGCTT TGCCACGGGACAAATATCTC |
| cloning | Ace(BamHI)R | D. suzukii | | GTGT GGATCC GTAGTAGTGCACGGAGGCGC |
| cloning | Ace(EcoRI)R | D. suzukii | | GTGT GAATTC GTAGTAGTGCACGGAGGCGC |
| cloning | Blw(XbaI)F | D. suzukii | | GTGT TCTAGA ACGCCCTGATCATCTACGAC |
| cloning | Blw(HindIII)F | D. suzukii | | GTGT AAGCTT ACGCCCTGATCATCTACGAC |
| cloning | Blw(BamHI)R | D. suzukii | | GTGT GGATCC TGGAATGTAGGCGGACACATC |
| cloning | Blw(EcoRI)R | D. suzukii | | GTGT GAATTC TGGAATGTAGGCGGACACATC |
| cloning | Tub(XbaI)F | D. suzukii | | GTGTTCTAGAACGCTAAGTCGGAGGAC |
| cloning | Tub(HindIII)F | D. suzukii | | GTGTAAGCTTACGCTAAGTCGGAGGAC |
| cloning | Tub(BamHI)R | D. suzukii | | GTGT GGATCC ACAGTATTAACATACATGCG |
| cloning | Tub(EcoRI)R | D. suzukii | | GTGTGAATTCACAGTATTAACATACATGCG |
| cloning | Rpl19(XbaI)F | D. suzukii | | GTGT TCTAGA GGTCTGATCATCAAGAAGCCC |
| cloning | Rpl19(HindIII)F | D. suzukii | | GTGT AAGCTT GGTCTGATCATCAAGAAGCCC |
| cloning | Rpl19(BamHI)R | D. suzukii | | GTGT GGATCC AGGTGCCTGTCGATCTTCTTG |
| cloning | Rpl19(EcoRI)R | D. suzukii | | GTGT GAATTC AGGTGCCTGTCGATCTTCTTG |
| cloning | White intron F | D. melanogaster | | GTGTGGATCCGTGAGTTTCTATTCGCAG |
| cloning | White intron R | D. melanogaster | | GTGTGAATTCCTGAGTTTCAAAATTGGTA |
| cloning | Tub(T7)F | D. suzukii | | GAATAATACGACTCACTATAGGGAGAACGCTAAGTCGGAGGAC |
| cloning | Tub(T7)R | D. suzukii | | GAATAATACGACTCACTATAGGGAGAACAGTATTAACATACATGCG |
| cloning | vATPase(T7)F | D. suzukii | | GAATAATACGACTCACTATAGGGAGATGGAGCAGTACAAGGCC |
| cloning | vATPase(T7)R | D. suzukii | | GAATAATACGACTCACTATAGGGAGAAACAGGGCGTTACGAATC |

REFERENCES

1. Coy. M. R. et al. Gene silencing in adult *Aedes aegypti* mosquitoes through oral delivery of double-stranded RNA. *J Appl. Entomol.* 136, 741-748 (2012).
2. Jarosch, a. & Moritz, R. F. a. Systemic RNA-interference in the honeybee *Apis mellifera*: Tissue dependent uptake of fluorescent siRNA after intra-abdominal application observed by laser-scanning microscopy. *J Insect Physiol.* 57, 851-857 (2011).
3. Li, H. et al. Long dsRNA but not siRNA initiates RNAi in western corn rootworm larvae and adults. *J. Appl. Entomol.* 139, 432-445 (2015).

4. Zhang, J., Khan, S. A., Hasse, C. & Ruf, S. Full crop protection from an insect pest by expression of long double-stranded RNAs in plastids. *Science* (80-.). 347, (2015).
5. Copeland, J. M. et al. Extension of *Drosophila* Life Span by RNAi of the Mitochondrial Respiratory Chain. *Curr. Biol.* 19, 1591-1598 (2009).
6. Zhang, H., Li, H., Guan, R. & Miao, X. Lepidopteran insect species-specific, broad spectrum, and systemic RNA interference by spraying dsRNA on larvae. *Entomol. Exp. Appl.* n/a-n/a (2015). doi:10.1111/eea.12300 482
7. Chen. A., Zheng. W., Zheng, W. & Zhang, H. The effects of RNA interference targeting *Bactrocera dorsalis* ds-Bdrpl19 on the gene expression of rpl19 in non-target insects. *Ecotoxicology* 24, 595-603 (2015).
8. Obbard, D. J., Gordon, K. H. J., Buck, A. H. & Jiggins, F. M. The evolution of RNAi as a defence against viruses and transposable elements. *Philos. Trans. R. Soc. Lond. B. Biol. Sci.* 364, 99-115 (2009).
9. Kim, D. H. & Rossi, J. J. RNAi mechanisms and applications. 44, 613-616 (2009).
10. Zotti, M. J. & Smagghe, G. RNAi Technology for Insect Management and Protection of Beneficial Insects from Diseases: Lessons, Challenges and Risk Assessments. *Neotrop. Entomol.* (2015). doi: 10.1007/s13744-015-0291-8
11. Burand, J. P. & Hunter, W. B. RNAi: Future in insect management. *J. Invertebr. Pathol.* 112, (2013).
12. San Miguel, K. & Scott, J. G. The next generation of insecticides: dsRNA is stable as a foliar-applied insecticide. *Pest Manag. Sci.* n/a-n/a (2015). doi: 10.1002/ps.4056
13. Li, H., Guan, R., Guo, H. & Miao, X. New insights into an RNAi approach for plant defence against piercing-sucking and stem-borer insect pests. *Plant. Cell Environ.* n/a-n/a (2015). doi:10.1111/pce.12546
14. Tian, H. et al. Developmental control of a lepidopteran pest *Spodoptera exigua* by ingestion of bacteria expressing dsRNA of a non-midgut gene. *PLoS One* 4, (2009).
15. Taracena, M. L. et al. Genetically Modifying the Insect Gut Microbiota to Control Chagas Disease Vectors through Systemic RNAi. *PLoS Negl. Trop. Dis.* 9, e0003358 (2015).
16. Starmer, W. T. A Comparison of *Drosophila* Habitats According to the Physiological Attributes of the Associated Yeast Communities. *Soc. Study Evol.* 35, 38-52 (2013).
17. Becher. P. G. et al. Yeast, not vinegar volatiles mediate *Drosophila melanogaster* attraction, oviposition and development. *Funct. Ecol.* 26, 822-828 (2012).
18. Scheidler. N. H., Liu, C., Hamby, K. A., Zalom, F. G. & Syed, Z. Volatile codes: Evolution of olfactory signals and reception in. *Sci. Rep.* in press
19. Palanca, L., Gaskett, A. C., Giinther, C. S., Newcomb, R, D. & Goddard, M. R. Quantifying Variation in the Ability of Yeasts to Attract *Drosophila melanogaster*. *PLoS One* 8, 1-10 (2013).
20. Starmer, W. T., Peris, F. & Fontdevila, A. The transmission of yeasts by *Drosophila buzzatii* during courtship and mating. *Anim. Behav.* 36, 1691-1695 (1988).
21. Coluccio, A. E., Rodriguez, R. K., Kernan, M. J. & Neiman, A. M. The yeast spore wall enables spores to survive passage through the digestive tract of *Drosophila*. *PLoS One* 3, 516 (2008).
22. Lee, J. C. et al. The susceptibility of small vinegars and cherries to the spotted-wing *drosophila, Drosophila suzukii*. *Pest Manag. Sci.* 67, 1358-1367 (2011).
23. Asplen, M. K., Anfora, G. & Biondi, A. Invasion biology of spotted wing *Drosophila* (*Drosophila suzukii*): a global perspective and future priorities. *J Pest SC* (2015). doi: 10.1007/s10745-006-9094-1
24. Walsh, D. B. et al. *Drosophila suzukii* (Diptera: Drosophilidae): Invasive Pest of Ripening Soft Vinegar Expanding its Geographic Range and Damage Potential. *J. Integr. Pest Manag.* 2, 1-7 (2011).
25. Bolda, M. P., Goodhue, R. E. & Zalom, F. G. Spotted Wing *Drosophila*: Potential Economic Impact of a Newly Established Pest. *Agric. Resour Econ. Updat. Univ. California. Giannini Found.* 13, 5-8 (2010).
26. Chiu, J. C. et al. Genome of *Drosophila suzukii*, the Spotted Wing *Drosophila*. *G3-Genes Genomes Genet.* 3, 2257-2271 (2013).
27. Iglesias, L. E., Nyoike, T. W. & Liburd. O. E. Effect of Trap Design, Bait Type, and Age on Captures of *Drosophila suzukii* (Diptera: Drosophilidae) in Berry Crops. *Hortic. Entomol.* 1508-1518 (2014).
28. Hamby, K. a., Hernández, A., Boundy-Mills, K. & Zalom, F. G. Associations of yeasts with spotted-wing *Drosophila* (*Drosophila suzukii*, Diptera: Drosophilidae) in cherries and raspberries. *Appl. Environ. Microbiol.* 78, 4869-4873 (2012).
29. Mao, J. & Zeng, F. Feeding-Based RNA Interference of a Gap Gene Is Lethal to the Pea Aphid, *Acyrthosiphon pisum*. *PLoS One* 7, 1-7 (2012).
30. Walshe, D. P., Lehane, S. M., Lehane, M. J. & Haines, L. R. Prolonged gene knockdown in the tsetse fly *Glossina* by feeding double stranded RNA. *Insect Mol. Biol.* 18, 11-19 (2009).
31. Wuriyanghan. H., Rosa, C. & Falk, B. W. Oral delivery of double-stranded RNAs and siRNAs induces RNAi effects in the potato/tomato psyllid. *Batericerca cockerelli*. *PLoS One* 6, (2011).
32. Baum, J. a et al. Control of coleopteran insect pests through RNA interference. *Nat. Biotechnol.* 25, 1322-1326 (2007).
33. Jackson, A. L. & Linsley, P. S. Noise amidst the silence: Off-target effects of siRNAs?*Trends Genet.* 20, 521-524 (2004).
34. Altschul, S., Gish, W. & Miller, W. Basic Local Alignment Search Tool. *J Mol Biol.* 215, 403-410 (1990).
35. Roignant, J.-Y. et al. Absence of transitive and systemic pathways allows cell-specific and isoform-specific RNAi in *Drosophila*. *RNA* 9, 299-308 (2003).
36. Li. X., Zhang, M. & Zhang, H. RNA interference of four genes in adult *Bactrocera dorsalis* by feeding their dsRNAs. *PLoS One* 6, (2011).
37. Harrison, B. R., Yazgan, O. & Krebs, J. E. Life without RNAi: noncoding RNAs and their functions in *Saccharomyces cerevisiae*. *Biochem. Cell Biol.* 87, 767-779 (2009).
38. Wang. J., Lu, Z., Wientjes, M. G. & Au, J. L.-S. Delivery of siRNA therapeutics: barriers and carriers. *AAPS J.* 12, 492-503 (2010).
39. Lopez, G. & Anderson, J. C. Synthetic Auxotrophs with Ligand-Dependent Essential Genes for a BL21(DE3) Biosafety Strain. *ACS Synth. Biol.* 21, 150615074302001 (2015).
40. Hokanson. K. E., Dawson, W. O., Handler, a. M., Schetelig, M. F. & St. Leger, R. J. Not all GMOs are crop plants: non-plant GMO applications in agriculture. *Transgenic Res.* 1-12 (2013). doi: 10.1007/s11248-013-9769-5

41. Svoboda, P. Off-targeting and other non-specific effects of RNAi experiments in mammalian cells. *Curr. Opin. Mol. Ther.* 9, 248-257 (2007).
42. Robbins, M., Judge, A. & MacLachlan, I. siRNA and innate immunity. *Oligonucleotides* 19, 89-102 (2009).
43. Lemaire, P. a, Anderson, E., Larv, J. & Cole, J. L. NIH Public Access. *Cell* 381, 351-360 (2009).
44. Chintapalli, V. R., Wang, J. & Dow, J. a T. Using FlyAtlas to identify better *Drosophila melanogaster* models of human disease. *Nat. Genet.* 39, 715-720 (2007).
45. Larkin, M. a. et al. Clustal W and Clustal X version 2.0. *Bioinformatics* 23, 2947-2948 (2007).
46. Boutros, M. et al. Genome-wide RNAi analysis of growth and viability in *Drosophila* cells. *Science* 303, 832-835 (2004).
47. Chiu. J. C., Low, K. H., Pike, D. H., Yildirim, E. & Edery, I. Assaying locomotor activity to study circadian rhythms and sleep parameters in *Drosophila*. *J. Vis. Exp.* 1-8 (2010). doi:10.3791/2157

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11117938B2). An electronic copy of the "Sequence Listing" will also be available from the USPTO upon request and payment of the fee set forth in 37 CFR 1.19(b)(3).

What is claimed is:

1. A method for controlling an insect pest, the method comprising contacting the insect pest with a composition comprising a yeast cell comprising a nucleic acid encoding a dsRNA molecule which specifically inhibits expression of a target gene in the insect pest, thereby controlling the insect pest, wherein the insect pest is *Drosophila suzukii* and the target gene is y-tubulin 23 C (yTub23C) gene.

2. The method of claim 1, wherein the yeast cell is killed.

3. The method of claim 1, wherein the yeast cell is living.

4. The method of claim 1, wherein the composition comprising the yeast cell is present in a lure trap.

5. The method of claim 1, wherein the yeast cell is *Saccharomyces cerevisiae*.

6. The method of claim 1, wherein the yeast cell is *Hanseniaspora uvarum*.

7. The method of claim 1 wherein the dsRNA molecule targets the 3' untranslated region of the yTub23C gene.

8. The method of claim 1, wherein the dsRNA target sequence is at least 90% identical to SEQ ID NO: 4.

9. A composition comprising a yeast cell comprising an expression cassette comprising a yeast promoter operably linked to a DNA sequence encoding a dsRNA molecule which specifically inhibits expression of a target gene in *Drosophila suzukii*, wherein the target gene is y-tubulin 23 C (yTub23C) gene.

10. The composition of claim 9, wherein the yeast cell is killed.

11. The composition of claim 9, wherein the yeast cell is living.

12. The composition of claim 9, wherein the yeast cell is *Saccharomyces cerevisiae*.

13. The composition of claim 9, wherein the yeast promoter is a bacteriophage T7 promoter or a TEF1 polymerase promoter.

14. The composition of claim 9, wherein the yeast cell is *Hanseniaspora uvarum*.

15. The composition of claim 9, wherein the dsRNA molecule targets the 3' untranslated region of the yTub23C gene.

16. The composition of claim 9, wherein the dsRNA target sequence is at least 90% identical to SEQ ID NO: 4.

17. The composition of claim 9, which is present in a lure trap.

18. An expression cassette comprising a yeast promoter operably linked to a DNA sequence encoding a double stranded RNA (dsRNA) which specifically inhibits expression of a target gene in an insect pest, wherein the target gene is a yTub23C gene.

19. The expression cassette of claim 18, wherein the yeast promoter is a bacteriophage T7 promoter or a TEF1 promoter.

20. The expression cassette of claim 18, wherein the yeast promoter is an inducible promoter.

21. The expression cassette of claim 18, wherein the dsRNA molecule targets the 3' untranslated region of the yTub23C gene.

22. The expression cassette of claim 18, wherein the dsRNA target sequence is at least 90% identical to SEQ ID NO: 4.

* * * * *